United States Patent [19]

Patmore

[11] Plant 4,684

[45] Apr. 7, 1981

[54] GREEN ASH TREE

[75] Inventor: Richard H. Patmore, Brandon, Canada

[73] Assignee: Jacob J. Driedger, Brandon, Canada

[21] Appl. No.: 34,153

[22] Filed: Apr. 27, 1979

[51] Int. Cl.[3] ..... A01H 5/12

[52] U.S. Cl. ..... Plt./51

[58] Field of Search ..... Plt./51

*Primary Examiner*—Robert E. Bagwill

*Attorney, Agent, or Firm*—Klarquist, Sparkman, Campbell, Leigh, Hall & Whinston

[57] ABSTRACT

This invention relates to a novel variety of Green Ash Tree, distinguished primarily by its glossy dark green foliage, seedlessness, and hardiness in severe northern climates.

1 Drawing Figure

DESCRIPTION

The present invention relates to a new and distinct variety of ash tree of the species botanically known as *Fraxinus pennsylvanica lanceolata* and commonly called "Green Ash". My new tree has now been named Patmore Ash. I discovered my new variety as a seedling mutation of unknown parentage which was growing in a cultivated area along a street in Vegreville, Alberta, Canada.

My attention was attracted to the new seedling because of its distinctive appearance caused by its dark green shiny leaves. This foliage made my tree decidedly different from other trees of this species which typically have a dull appearing leaf which is a more pale green color. Close observation of the new seedling and continued observations of the progeny thereof, subsequently asexually propagated by persons under my direction in Canada by budding on seedling ash understock, confirmed that the unique foliage of my new variety was the result of a seedling variation.

I am, therefore, convinced that my new tree represents a new and improved variety of Green Ash Tree, as particularly evidenced by the following unique combination of characteristics which have proven firmly fixed, are outstanding therein, and which distinguish it from all other varieties of this species:

(1) glossy dark green leaves;

(2) seedlessness;

(3) leaves which appear earlier in the growing season than those of other varieties and which are retained longer;

(4) leaves that are more deeply serrated than normal for the species; and (5) resistance to winter kill in severe northern climates.

The accompanying photographs depict the color of the foliage of my new variety as nearly true as is reasonably possible to make the same in color illustrations of this character.

FIG. 1 is a color photograph of the tree of the present invention showing the appearance of the entire tree;

FIG. 2 is a color photograph of leaves of the tree of my invention; and

FIG. 3 is a color photograph of a single leaflet of the tree of my invention showing its glossy upper surface.

As previously indicated, the leaves of my new variety are dark green and extremely glossy. In addition, they maintain this glossy characteristic throughout the growing season. In contrast, other Green Ash Trees have leaves which have a dull appearance and which are a lighter green color. In addition, the leaves of my variety are more deeply serrated than normal for the species. The serrations of leaves of my tree appear almost twice as deep as other trees of the species. In addition, the margins of leaves of my tree have a consistent pattern of serrations while seedling ash trees of the species have irregular serrations.

Also, the flowers of my new variety are staminate so that my tree is seedless. Consequently, when planted in parks and other areas, my tree will not produce unwanted seedlings that would have to be removed at some expense.

In addition, observations of my tree have convinced me that it is hardier than other cultivars of the species and also resistant to blight. For that matter, it is the only seedless Green Ash tree cultivar I know of that is hardy in the severe climate of the Canadian Prairie Provinces (Saskatchewan, Alberta and Manitoba).

In contrast, varieties such as the Marshalls Seedless Green Ash are susceptible to winter kill during an unfavorable winter in these northern climates. However, the Green Ash tree which is native to the Canadian Prairie Provinces exhibits hardiness comparable to my new Green Ash tree.

This combination of seedlessness, hardiness, and dark green glossy foliage makes my tree extremely useful for ornamental purposes.

I have observed that leaves appear on my tree approximately ten days sooner than on other ash trees of this species, including Green Ash trees native to the Canadian Prairie Provinces, of which I am aware. In addition, my tree retains its leaves approximately ten days to two weeks longer than these other trees.

Adding to the ornamental appearance of my tree is its erect trunk and evenly branched crown. The branches of my tree ascend upwardly from the trunk with the branches having an upward curvature which further enhances the appearance of my tree.

Although I have not made any specific comparisons of the growth rate of my new variety to other varieties of this species, I believe my new tree is somewhat faster growing. In 1975, I did observe one block of about six or seven hundred of my trees. These trees were two years old from the time of budding, had branched, and were consistently six to seven feet tall. Also, insofar as I have observed, the remaining characteristics of my tree are like those of other Green Ash trees.

The following is a detailed description of my new variety of Green Ash tree, with color terminology in accordance with the "Royal Horticultural Society Color Chart" (hereinafter R.H.S.), published by the Royal Horticultural Society of London.

Parentage: a seedling mutation of unknown parentage.

Propagation: holds distinguishing characteristics through propagation by budding on seedling ash understock.

Locality where grown and observed: Vegreville, Alberta, Canada; Patmore Nursery in Brandon, Manitoba, Canada; Agriculture Canada Research Station, Morden, Manitoba, Canada, and elsewhere.

Tree: erect trunk, evenly branched crown. Hardy in severe northern climates.

Branches: upwardly ascending with an upward curvature to its branches.

Foliage:

*Shape of leaf.*—Pinnate, with 5 to 7 leaflets per leaf.

*Shape of leaflet.*—Overall shape: lanceolate to elliptic. Apex: acute. Base: obtuse. Margin: serrate with serrations deeper than typical of the species. Appearance: smooth, glossy leaflets with a dark green coloration, the upper leaf summer color being like R.H.S. Plates 137A to 137B, the summer color of the underside of the leaf is like R.H.S. Plate 147B, the fall color of the upper surface of the leaf is like R.H.S. Plate 152D, and the fall color of the underside of the leaf is like R.H.S. Plate 152C.

*Size.*—Average leaf measurement, 19.5 cm long and 13.5 cm wide. Average terminal leaflet measurement, 9 cm long and 4.5 cm wide. Average side leaflet measurement, 7.5 cm long and 3.5 cm wide.

*Pubescence.*—There is a light pubescence on the lower leaflet mid rib and on the lower half of the leaflet blade.

Flowers: staminate.

I claim:

1. A new and distinct variety of Green Ash tree substantially as herein shown and described, characterized particularly as to novelty by seedlessness, dark green glossy leaves and hardiness in northern climates.

* * * * *

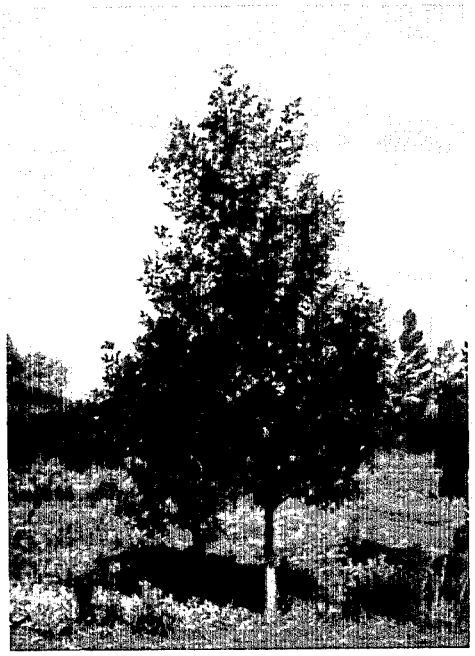
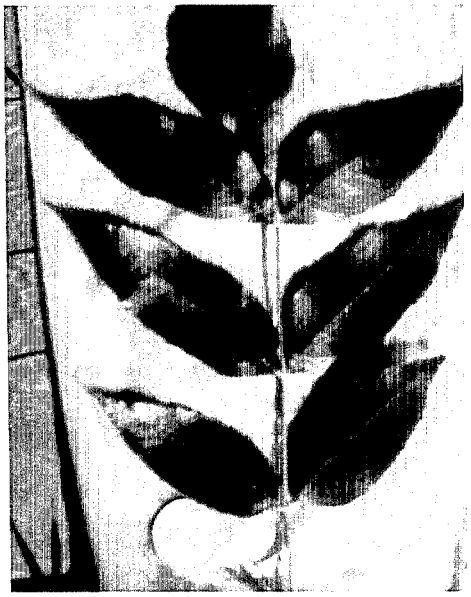
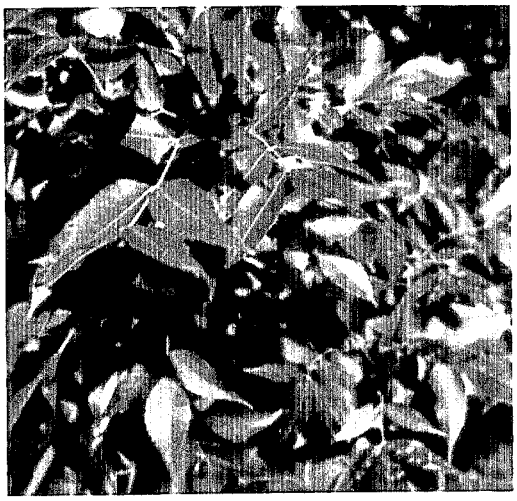

UNITED STATES PATENT AND TRADEMARK OFFICE

CERTIFICATE OF CORRECTION

PATENT NO. : PP. 4,684

DATED : April 7, 1981

INVENTOR(S) : RICHARD H. PATMORE

It is certified that error appears in the above-identified patent and that said Letters Patent are hereby corrected as shown below:

Column 4, line 22 after " . . . novelty by seedlessness,"

insert --early leaf appearance, . . .--.

Signed and Sealed this

*Eighteenth* Day of *August 1981*

[SEAL]

*Attest:*

GERALD J. MOSSINGHOFF

*Attesting Officer*

*Commissioner of Patents and Trademarks*